US011145824B2

(12) United States Patent
Hang et al.

(10) Patent No.: US 11,145,824 B2
(45) Date of Patent: Oct. 12, 2021

(54) ORGANIC PHOTOELECTRIC FUNCTIONAL MATERIAL, METHOD FOR PREPARING THE SAME, USE OF THE SAME, ORGANIC ELECTRONIC ASSEMBLY, AND LIGHT-EMITTING DEVICE

(71) Applicants: AAC Microtech (Changzhou) Co., Ltd., Changzhou (CN); Nanjing Tech University, Nanjing (CN)

(72) Inventors: Xiaochun Hang, Shenzhen (CN); Yin Zhang, Shenzhen (CN); Zhikuan Chen, Shenzhen (CN); Zhengyi Sun, Shenzhen (CN); Shaohai Chen, Saratoga, CA (US)

(73) Assignee: AAC Microtech(Changzhou)Co., Ltd., Changzhou (CN)

( * ) Notice: Subject to any disclaimer, the term of this patent is extended or adjusted under 35 U.S.C. 154(b) by 501 days.

(21) Appl. No.: 15/975,579

(22) Filed: May 9, 2018

(65) Prior Publication Data
US 2019/0237678 A1 Aug. 1, 2019

(30) Foreign Application Priority Data

Jan. 30, 2018 (CN) .......................... 201810090751.5

(51) Int. Cl.
| *C07D 215/04* | (2006.01) |
| *C07D 311/82* | (2006.01) |
| *H01L 51/00* | (2006.01) |
| *H01L 51/50* | (2006.01) |
| *C07D 215/06* | (2006.01) |
| *H01L 51/52* | (2006.01) |

(52) U.S. Cl.
CPC ........ *H01L 51/0072* (2013.01); *C07D 215/06* (2013.01); *H01L 51/0052* (2013.01); *H01L 51/0071* (2013.01); *H01L 51/5024* (2013.01); *H01L 51/5072* (2013.01); *H01L 51/5016* (2013.01); *H01L 51/5206* (2013.01); *H01L 51/5221* (2013.01); *H01L 2251/5384* (2013.01); *Y02B 20/00* (2013.01)

(58) Field of Classification Search
CPC .. C07D 215/04; C07D 215/12; C07D 215/14; H01L 51/0071
See application file for complete search history.

(56) References Cited

U.S. PATENT DOCUMENTS 9,184,396 B2 * 11/2015 Cheng .................... C09K 11/06
10,370,473 B2 * 8/2019 Nakayama ................ C08F 2/44

FOREIGN PATENT DOCUMENTS

KR 1408515 B1 * 6/2014

OTHER PUBLICATIONS

Boblak & Klumpp, JOC 2014, 79, 5852-5857.*
Machine-generated English-language translation of KR-1408515-B1.*
SciFinder Searches (Sep. 16, 2020).*

* cited by examiner

*Primary Examiner* — Vu A Nguyen
(74) *Attorney, Agent, or Firm* — IPro, PLLC; Na Xu

(57) ABSTRACT

The present disclosure relates to an organic photoelectric functional material, a method for the same, usage of the same, and a light-emitting device. The organic photoelectric functional material has electroluminescence and electron transportation properties. The organic photoelectric functional material is selected from a group consisting of compounds represented by formula I and formula II, and combinations thereof. If the organic photoelectric functional material is used as an electroluminescence material, light emission thereof can be adjusted by modifying a quinoline moiety thereof with a substituent, and a luminous range thereof is about 345 nm to about 700 nm. If the organic photoelectric functional material is used as an electron transporting-type host material which, together with hole-type host material, forms an exciplex co-host system, a (Continued)

light-emitting device prepared therefrom has improved stability and efficiency when compared with a light-emitting device prepared from a traditional host material.
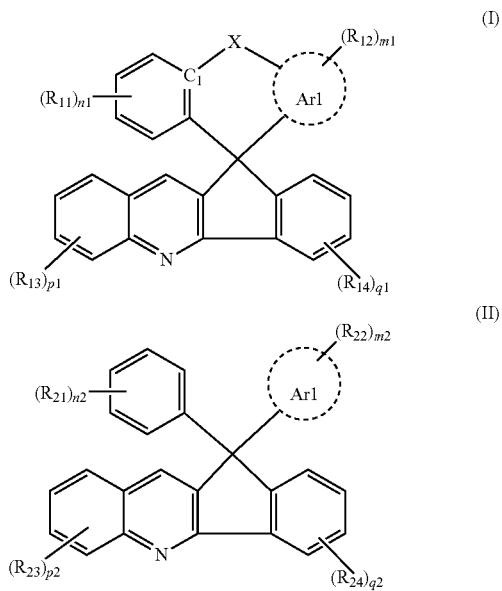
7 Claims, 1 Drawing Sheet

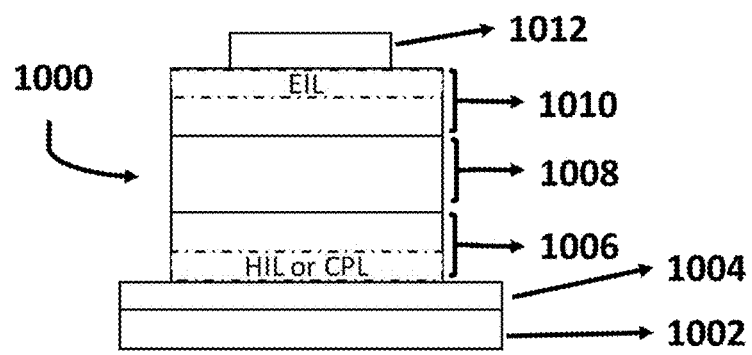

ORGANIC PHOTOELECTRIC FUNCTIONAL MATERIAL, METHOD FOR PREPARING THE SAME, USE OF THE SAME, ORGANIC ELECTRONIC ASSEMBLY, AND LIGHT-EMITTING DEVICE

TECHNICAL FIELD

The present disclosure relates to the field of organic light-emitting material technologies and, particularly, relates to an organic photoelectric functional material, a method for preparing the same, a use of the same, an organic electronic assembly, and a light-emitting device.

BACKGROUND

An organic light-emitting diode (OLED) refers to a luminescence phenomenon that luminescent materials such as small organic molecules, metal organic complex molecules or polymer molecules convert electrical energy directly into light energy under a forward bias electric field. OLED has drawn widespread attention in both academia and industry, due to its advantages of fast response, low driving voltage, high luminous efficiency, high resolution, high contrast, wide viewing angle, self-luminous characteristics, and requiring no backlight. Besides, OLED can also be produced on a cheap glass, metals or flexible plastics, and thus has advantages of low cost, simple production process, large scale production capability, etc. OLED has become a new generation of full-color display and lighting technology, and has a broad application prospect in full-color display and planar solid-state lighting field.

Luminescent materials IF d for early devices are mainly organic small molecule fluorescent materials which can only use molecules in electro excited singlet state, and the spin quantum statistics shows that theoretical internal quantum efficiency thereof is merely 25%. 75% of excited molecules are in an excited triplet state, and may emit phosphorescent light by radioactive transition back to ground state. It is generally difficult for small molecule organic compounds to emit phosphorescent light at room temperature until the discovery of the phosphorescence electroluminescence phenomenon of organometallic complex molecular materials at room temperature. The inter-system crossing (ISC) of electrons from a singlet state to a triplet state can be effectively prompted by the strong spin orbit coupling of heavy metal atoms, so that the OLED devices can fully use all singlet and triplet excitons, and the theoretical internal quantum efficiency of the luminescent materials can reach 100%. So far, the research of luminescent materials has entered a new period.

At present, the imbalanced carrier transportation is a problem in OLED devices. For example, mobility of electrons in electron transporting layer is several orders lower than mobility of holes in a hole transporting layer, and the imbalanced electron/hole transportation increases a turn-on voltage and reduces a service life of a phosphorescent OLED device.

In view of the above, the present disclosure is provided.

BRIEF DESCRIPTION OF DRAWINGS

The FIGURE illustrates a schematic diagram of a light-emitting device.

DESCRIPTION OF EMBODIMENTS

The present disclosure is further illustrated with reference to the following embodiments. It should be understood that all of the embodiments are merely intended to illustrate the present disclosure rather than to limit the present disclosure.

The embodiments of the present disclosure provide a new organic photoelectric functional material. The organic photoelectric functional material is selected from a group consisting of compounds represented by formula I and combinations thereof;

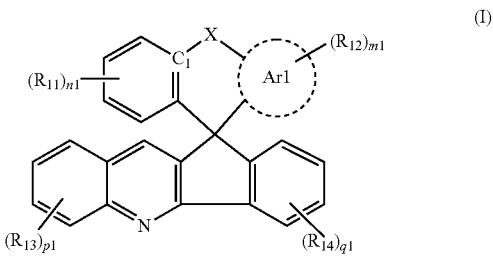

(I)

$R_{11}$, $R_{12}$, $R_{13}$ and $R_{14}$ each are independently selected from a group consisting of substituted or unsubstituted $C_1$-$C_{36}$ alkyl, substituted or unsubstituted $C_2$-$C_{36}$ alkenyl, substituted or unsubstituted $C_6$-$C_{36}$ aryl, substituted or unsubstituted $C_6$-$C_{36}$ heteroaryl, substituted or unsubstituted $C_3$-$C_{18}$ heteroalicyclic group, substituted or unsubstituted $C_1$-$C_{24}$ alkoxy, substituted or unsubstituted $C_1$-$C_{24}$ alkylthiol, substituted or unsubstituted $C_2$-$C_{24}$ alkenyloxy, substituted or unsubstituted $C_2$-$C_{24}$ alkynyloxy, substituted or unsubstituted $C_6$-$C_{36}$ aryloxy, substituted or unsubstituted $C_2$-$C_{24}$ alkoxycarbonyl, substituted or unsubstituted $C_2$-$C_{36}$ ester group, substituted or unsubstituted $C_2$-$C_{36}$ amido group, substituted or unsubstituted $C_1$-$C_{36}$ sulfonyl, substituted or unsubstituted $C_1$-$C_{36}$ sulfinyl, substituted or unsubstituted $C_1$-$C_{36}$ sulfonylamino group, substituted or unsubstituted $C_1$-$C_{36}$ phosphorylamino group, substituted or unsubstituted $C_2$-$C_{24}$ alkoxycarbonylamino group, substituted or unsubstituted $C_7$-$C_{37}$ aryloxycarbonylamino group, substituted or unsubstituted $C_1$-$C_{18}$ monoalkylamino group, substituted or unsubstituted $C_2$-$C_{36}$ dialkylamino group, substituted or unsubstituted $C_6$-$C_{18}$ monoarylamino group, and substituted or unsubstituted $C_6$-$C_{36}$ diarylamino group, wherein the substituents are selected from a group consisting of deuterium, halogen, hydroxyl, mercapto group, nitrogroup, cyano, amino-group, carboxyl, sulpho, diazanyl, carbamido, $C_1$-$C_6$ alkyl, and $C_6$-$C_{12}$ aryl;

adjacent two or more of $R_{11}$, $R_{12}$, $R_{13}$ and $R_{14}$ are capable of being interlinked into a ring;

Ar1 represents phenyl, α-naphthyl, or β-naphthyl;

X is present or is absent; if X is present, X represents —O—, —CH$_2$—, —NH—; if X is absent, $C_1$ is linked to Ar1 by a single bond; and m1, n1, p1 and q1 are independently an integer selected from a group consisting of 0, 1, 2, 3, and 4 when X is present. n1 is selected from a group consisting of 1, 2, 3, and 4 and m1, p1 and q1 each are independently an integer selected from a group consisting of 0, 1, 2, 3, and 4 when X is absent.

In the substituents:

The $C_{1-36}$ alkyl may be chain alkyl or cyclic alkyl, and hydrogen on the cyclic alkyl may be substituted by an alkyl, for example, methyl, ethyl, n-propyl, iso-propyl, n-butyl, iso-butyl, sec-butyl, tert-butyl, n-pentyl, iso-pentyl, sec-pentyl, neopentyl, hexyl, heptyl, semi radical, nonyl, decyl, dodecyl, tetradecyl, hexadecyl, eicosyl, tetracosyl, etc.

The $C_{2-36}$ alkenyl may be cyclic alkenyl or chain alkenyl. The number of double bond in the alkenyl may be one or more. Examples of the alkenyl at least include: vinyl, allyl, isopropenyl, pentenyl, cyclopropenyl, cyclobutenyl, cyclopentenyl, cyclopentadienyl, cyclohexenyl, cyclohexadienyl.

The $C_{6-36}$ aryl includes multi-phenyl formed by connecting multiple phenyls, and fused ring compounds formed by fusing two or more phenyls, for example: phenyl, naphthyl, biphenyl, etc.

The heterocyclic groups include heteroalicyclic groups and heteroaryl, and the heteroalicyclic groups are heterocyclic compounds without aromatic character, for example, azetidinyl, dioxolanyl. The heteroaryl refers to a monocyclic or polycyclic aromatic ring system, wherein at least one ring member is not carbon. Examples of the heteroaryl includes: furyl, imidazolyl, isothiazolyl, isoxazolyl, morpholinyl, oxazolyl (for example, 1,2,3-oxadiazolyl, 1,2,5-oxadiazolyl, 1,3,4-oxadiazolyl), piperazinyl, piperidyl, pyrazinyl, pyrazolyl, pyridazinyl, pyridyl, pyrimidyl, pyrryl, pyrrolidinyl, tetrahydrofuryl, tetrahydropyranyl, tetrazinyl (e.g., 1,2,4,5-tetrazinyl), tetrazolyl (e.g., 1,2,3,4-tetrazolyl, 1,2,4,5-tetrazolyl), thiadiazoly (e.g., 1,2,3-thiadiazoly, 1,2,5-thiadiazoly, and 1,3,4-thiadiazoly), thiazolyl, thienyl, triazinyl (e.g., 1,3,5-triazinyl, 1,2,4-triazinyl), triazolyl (e.g., 1,2,3-triazolyl, 1,3,4-triazolyl), etc.

If the mentioned alkyl contains an oxygen atom, the alkyl may be alkoxy. If the mentioned alkenyl contains an oxygen atom, the alkenyl may be alkenyloxy. If the mentioned aryl contains an oxygen atom, the aryl may be aryloxy.

The alkoxycarbonyl is represented by —O—C(=O)—R', wherein R' is the alkyl mentioned in the present disclosure.

The sulfonyl is represented by —S(=O)$_2$R', and the sulfinyl is represented as —S(=O)—R', wherein R' is the alkyl, alkoxy, alkenyl, alkynyl, aryl, heteroaryl, or the like mentioned in the present disclosure.

The sulfonylamino group is represented by —S(=O)$_2$—NH—R' or —S(=O)$_2$—NR'R", wherein R' and R" each are independently the alkyl, alkoxy, alkenyl, alkynyl, aryl, heteroaryl or the like mentioned in the present disclosure.

The amido group is represented by —C(=O)—NH—R' or —S(=O)$_2$—NR'R", wherein R' and R" each are independently the alkyl, alkoxy, alkenyl, alkynyl, aryl, heteroaryl, or the like mentioned in the present disclosure.

The phosphorylamino group is represented by —P(=O)$_2$—NH—R' or —P(=O)$_2$—NR'R", wherein R' and R" each are independently the alkyl, alkoxy, alkenyl, alkynyl, aryl, heteroaryl, or the like mentioned in the present disclosure.

The alkoxycarbonylamino group is represented by —O—C(=O)— NH—R' or —O—C(=O)— NR'R", wherein R' and R" are independently the alkyl mentioned in the present disclosure.

The aryloxycarbonylamino group is represented by —O—C(=O)— NH—R' or —O—C(=O)— NR'R", wherein R' and R" are independently the aryl mentioned in the present disclosure.

The dialkylamino group is represented as —NR'R", wherein R' and R" are independently the alkyl mentioned in the present disclosure.

The monoalkylamino group is represented as —NH—R', wherein R' is the alkyl mentioned in the present disclosure.

The diarylamino group is represented as —NR'R", wherein R' and R" are independently the aryl mentioned in the present disclosure.

The monoarylamino group is represented as —NH—R', wherein R' is the aryl mentioned in the present disclosure.

The ester group is represented as —C(=O)—O—R", wherein R' is the alkyl, alkenyl, alkynyl, aryl, heteroaryl, or the like mentioned in the present disclosure.

The halogen may be fluorine, chlorine, bromine and iodine.

The new organic photoelectric functional material provided by the present disclosure has properties of electroluminescence and electron transporting, and thus can be applied in the organic electroluminescence field. If the organic photoelectric functional material is used as an electroluminescence material, light emission of the organic photoelectric functional material can be adjusted to a luminous range of about 345 nm to about 700 nm by modifying a quinoline moiety thereof with a substituent. The compounds provided by the present disclosure may be used as fluorescent light-emitting materials, delayed fluorescent light-emitting materials, or phosphorescent light-emitting material. If the organic photoelectric functional material is used as an electron transporting-type host material which, together with the hole-type host material, forms an exciplex co-host system, a light-emitting device prepared therefrom has improved stability and efficiency when compared with a light-emitting device prepared from a traditional host material. As mentioned above, the imbalanced carrier transportation problem exists in the OLED devices at present. An exciplex formed by two host materials, or a combination of a host material and a doping material is effective solutions for solving the imbalanced hole/electron transportation problem. In the related art, compound molecules containing a quinoline structure are widely applied in a hole injection layer and an electron transporting layer of the OLED device. For example, both 8-Hydroxyquinolinolato-lithium (LiQ) and 8-hydroxylquinolinolato-aluminum (Alq$_3$) have chemically stable quinoline core structure, and an OLED device prepared therefrom has high electron mobility from a cathode to a light-emitting layer under a certain driving voltage. It is found in researches that a photoelectric functional compound is formed by modifying the quinoline c with substituent, or by further forming a spiro structure based on the quinoline structure. Due to electroluminescence property and electron transportation property of the photoelectric functional compound, on the one hand, the photoelectric functional compound can be used as a fluorescent emitter, a delayed fluorescent emitter, or a phosphorescent emitter; on the other hand, the photoelectric functional compound can be independently used as a bipolar host material, or as an electron transporting-type host material which, together with a hole-type host material, forms an exciplex as a co-host system, thereby overcoming the imbalanced carrier transportation problem in the OLED device.

In an embodiment, the organic photoelectric functional material of the present disclosure is used as the electron transporting-type host material in a co-host system, whose stability and efficiency is advantageous over a traditional C—N bonding structure, for example, 1,3,5-tris(1-phenyl-1H-benzimidazole-2-yl) benzene (TPBi). In addition, the organic photoelectric functional material of the present disclosure and a hole transporting material form an exciplex, the hole transporting material having LUMO is at least 0.1 eV higher than the organic photoelectric functional material. Examples of the hole transporting material include 4,4',4"-tris(carbazole-9-yl) triphenylamine (TCTA), 3,3'-di(N-carbazolyl)-1,1'-biphenyl (mCP), etc. The luminous range of the formed exciplex is 445 nm to 700 nm.

As an improvement of the organic photoelectric functional material of the present disclosure, the organic photoelectric functional material is selected from a group consisting of compounds represented by formula IA, compounds represented by IB, compounds represented by IC, compounds represented by ID, and combinations thereof;

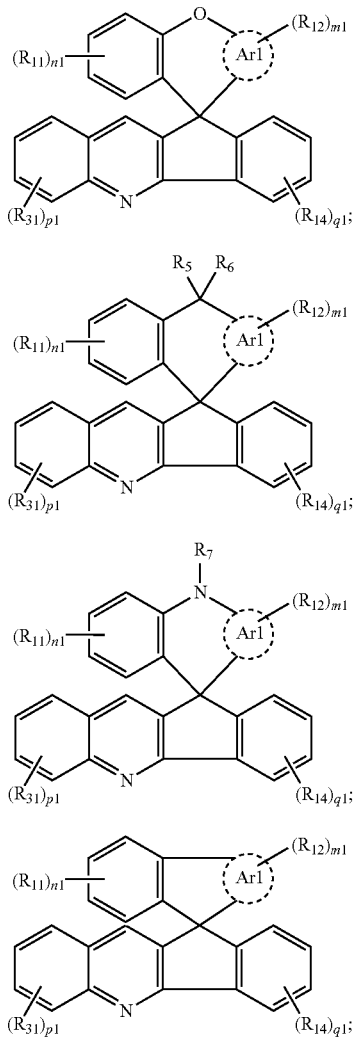

wherein $R_5$, $R_6$, and $R_7$ each are independently selected from a group consisting of substituted or unsubstituted $C_1$-$C_{36}$ alkyl, substituted or unsubstituted $C_2$-$C_{36}$ alkenyl, substituted or unsubstituted $C_6$-$C_{36}$ aryl, substituted or unsubstituted $C_6$-$C_{36}$ heteroaryl, substituted or unsubstituted $C_3$-$C_{18}$ heteroalicyclic group, substituted or unsubstituted $C_1$-$C_{24}$ alkoxy, substituted or unsubstituted $C_1$-$C_{24}$ alkylthiol, substituted or unsubstituted $C_2$-$C_{24}$ alkenyloxy, substituted or unsubstituted $C_2$-$C_{24}$ alkynyloxy, substituted or unsubstituted $C_6$-$C_{36}$ aryloxy, substituted or unsubstituted $C_2$-$C_{24}$ alkoxycarbonyl, substituted or unsubstituted $C_2$-$C_{36}$ ester group, substituted or unsubstituted $C_2$-$C_{36}$ amido group, substituted or unsubstituted $C_1$-$C_{36}$ sulfonyl, substituted or unsubstituted $C_1$-$C_{36}$ sulfinyl, substituted or unsubstituted $C_1$-$C_{36}$ sulfonylamino group, substituted or unsubstituted $C_1$-$C_{36}$ phosphorylamino group, substituted or unsubstituted $C_2$-$C_{24}$ alkoxycarbonylamino group, substituted or unsubstituted $C_7$-$C_{37}$ aryloxycarbonylamino group, substituted or unsubstituted $C_1$-$C_{18}$ monoalkylamino group, substituted or unsubstituted $C_2$-$C_{36}$ dialkylamino group, substituted or unsubstituted $C_6$-$C_{18}$ monoarylamino group, substituted or unsubstituted $C_6$-$C_{36}$ diarylamino group, wherein the substituents are selected from a group consisting of deuterium, halogen, hydroxyl, mercapto group, nitro-group, cyano, amino-group, carboxyl, sulpho, diazanyl, carbamido, $C_1$-$C_6$ alkyl, and $C_6$-$C_{12}$ aryl; and adjacent two or more of $R_{11}$, $R_{12}$, $R_{13}$, $R_{14}$, $R_5$, $R_6$, and $R_7$ are capable of being interlinked into a ring.

As an improvement of the organic photoelectric functional material of the present disclosure, the organic photoelectric functional material represented by formula IA is selected from a group consisting of compounds represented by formula IA1 and combinations thereof,

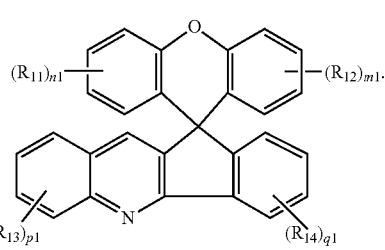

As an improvement of the organic photoelectric functional material of the present disclosure, the organic photoelectric functional material represented by formula IB is selected from a group consisting of compounds represented by formula IB1 and combinations thereof,

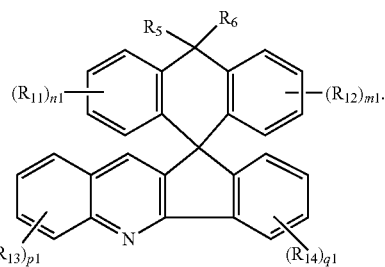

As an improvement of the organic photoelectric functional material of the present disclosure, the organic photoelectric functional material represented by formula IC is selected from a group consisting of compounds represented by formula IC1, compounds represented by formula IC2, and combinations thereof,

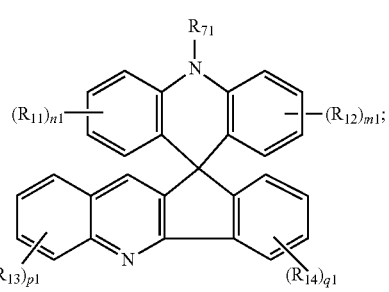

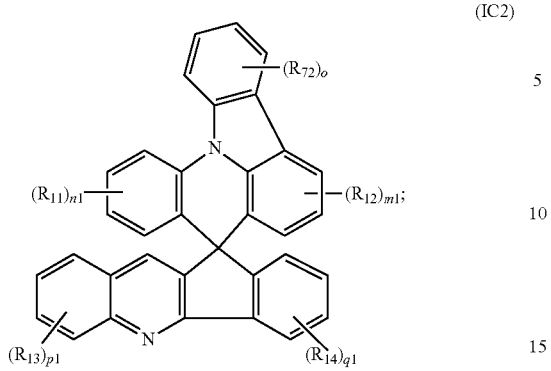

(IC2)

wherein $R_{71}$ and $R_{72}$ each are independently selected from a group consisting of substituted or unsubstituted $C_1$-$C_{36}$ alkyl, substituted or unsubstituted $C_2$-$C_{36}$ alkenyl, substituted or unsubstituted $C_6$-$C_{36}$ aryl, substituted or unsubstituted $C_6$-$C_{36}$ heteroaryl, substituted or unsubstituted $C_3$-$C_{18}$ heteroalicyclic group, substituted or unsubstituted $C_1$-$C_{24}$ alkoxy, substituted or unsubstituted $C_1$-$C_{24}$ alkylthiol, substituted or unsubstituted $C_2$-$C_{24}$ alkenyloxy, substituted or unsubstituted $C_2$-$C_{24}$ alkynyloxy, substituted or unsubstituted $C_6$-$C_{36}$ aryloxy, substituted or unsubstituted $C_2$-$C_{24}$ alkoxycarbonyl, substituted or unsubstituted $C_2$-$C_{36}$ ester group, substituted or unsubstituted $C_2$-$C_{36}$ amido group, substituted or unsubstituted $C_1$-$C_{36}$ sulfonyl, substituted or unsubstituted $C_1$-$C_{36}$ sulfinyl, substituted or unsubstituted $C_1$-$C_{36}$ sulfonylamino group, substituted or unsubstituted $C_1$-$C_{36}$ phosphorylamino group, substituted or unsubstituted $C_2$-$C_{24}$ alkoxycarbonylamino group, substituted or unsubstituted $C_7$-$C_{37}$ aryloxycarbonylamino group, substituted or unsubstituted $C_1$-$C_{18}$ monoalkylamino group, substituted or unsubstituted $C_2$-$C_{36}$ dialkylamino group, substituted or unsubstituted $C_6$-$C_{18}$ monoarylamino group, and substituted or unsubstituted $C_6$-$C_{36}$ diarylamino group, wherein the substituents are selected from a group consisting of deuterium, halogen, hydroxyl, mercapto group, nitro-group, cyano, amino-group, carboxyl, sulpho, diazanyl, carbamido, $C_1$-$C_6$ alkyl, and $C_6$-$C_{12}$ aryl;

adjacent two or more of $R_{11}$, $R_{12}$, $R_{13}$, and $R_{14}$ are capable of being linked into a ring; and the o is an integer selected from a group consisting of 0, 1, 2, 3, and 4.

As an improvement of the organic photoelectric functional material of the present disclosure, the organic photoelectric functional material is selected from a group consisting of the following compounds:

Compound 3

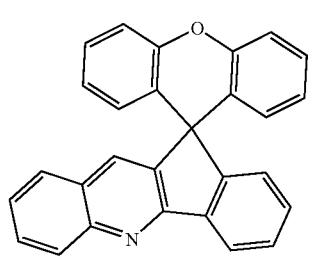

Compound 4

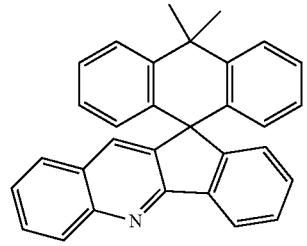

Compound 5

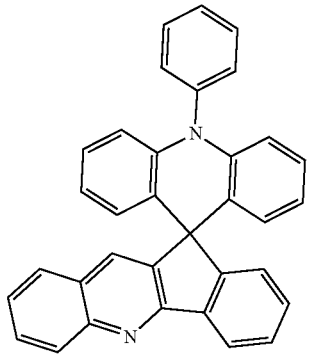

Compound 6

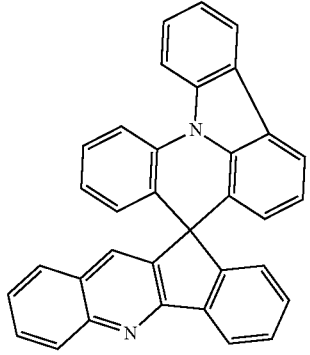

Compound 7

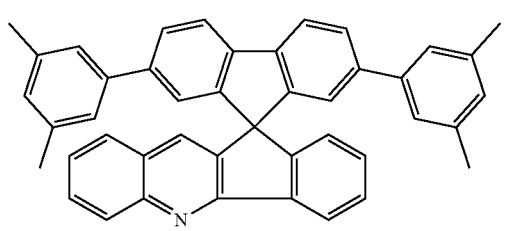

Compound 10

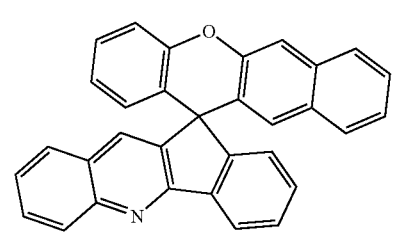

-continued

Compound 11

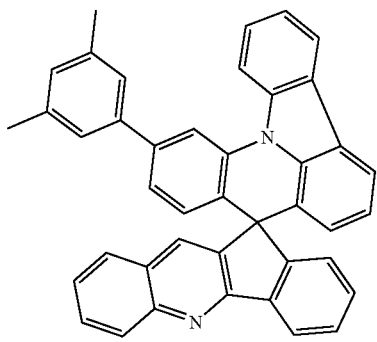

Compound 12

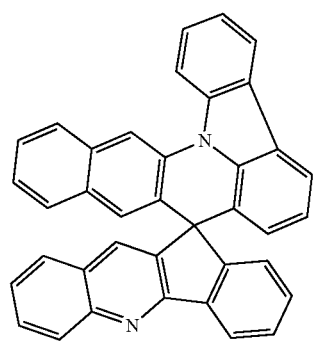

Methods for preparing the compounds of the present disclosure are illustrated in the embodiments below. These methods are merely exemplary but not intended to limit the present disclosure. Based on these methods, those skilled in the art can modify these methods and obtain other methods for preparing the compounds of the present disclosure without departing from the invention concept of the present disclosure. The other methods obtained shall also fall into protection scope of the present disclosure. The temperature, catalyst, concentration, composition of the reactants, and other process conditions may be varied, and those skilled in the art can select suitable reactants and reaction conditions for a specific compound to be prepared, based on the disclosed contents in the present disclosure.

Method of measurement. in deuterated chloroform ($CDCl_3$) or deuterated dimethyl sulfoxide ($DMSO-d^6$) solution, spectrums of $^1$H-NMR (H-nuclear magnetic resonance) and $^{13}$C-NMR (C-nuclear magnetic resonance) are recorded by Varian liquid nuclear magnetic resonance spectrometer, where the resonant frequency is 300, 400, or 500 MHz, and the chemical shift is based on the residual protonated solvent. If $CDCl_3$ is used as the solvent, tetramethylsilane (S=0.00 ppm) is used as an internal reference to record $^1$H-NMR (H-nuclear magnetic resonance) spectrum, and $CDCl_3$ ($\delta$=77.00 ppm) is used an internal reference to record $^{13}$C-NMR (C-nuclear magnetic resonance) spectrum. If $DMSO-d^6$ is used as the solvent, the residual $H_2O$ ($\delta$=3.33 ppm) is used as an internal reference to record $^1$H-NMR (H-nuclear magnetic resonance) spectrum, and $DMSO-d^6$ ($\delta$=39.52 ppm) is used as an internal reference to record $^{13}$C-NMR (C-nuclear magnetic resonance) spectrum. The abbreviations (or combinations thereof) below are used to illustrate diversity of $^1$H-NMR (H-nuclear magnetic resonance): s=singlet, d=doublet, t=triplet, q=quartet, p=quintuplet, m=multiplet, br=width.

In an embodiment, a method for preparing compounds represented by formula I at least includes the following steps:

step 1: preparing precursors represented by formula A and formula B; and step 2: performing nucleophilic addition reaction of the precursors represented by formula A and formula B, and then performing dehydrocyclization to obtain the compounds represented by formula I.

or step 1: preparing precursors represented by formula C and formula D; and step 2: performing nucleophilic addition reaction of the precursors represented by formula C and formula D, and then performing dehydrocyclization to obtain the compounds presented by formula I.

The chemical equations are shown as follows:

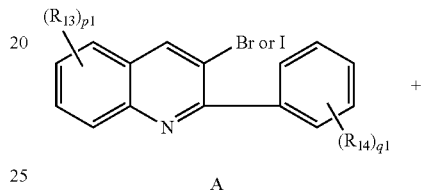

A

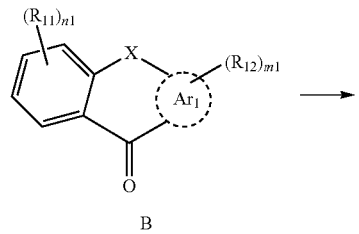

B

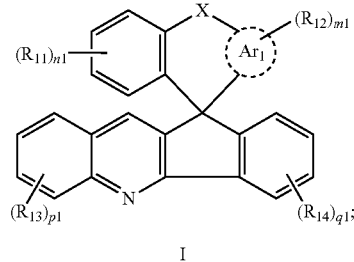

I

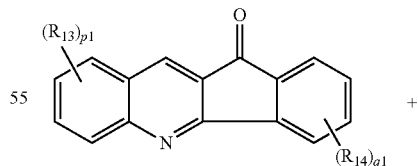

C

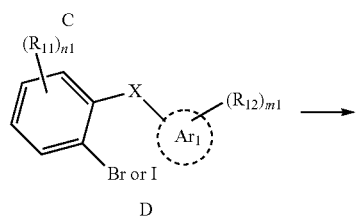

D

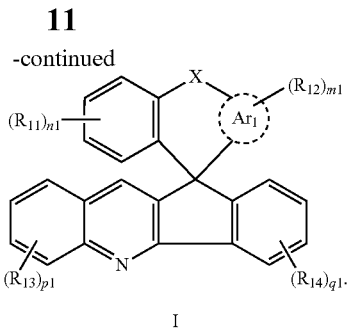

I

Synthesis Example 3: Synthesis of Compound 3

(1) Synthesis of the precursor 9-(2-phenylquinoline-3-yl)-9H-9-hydroxy Xanthene of Compound 3

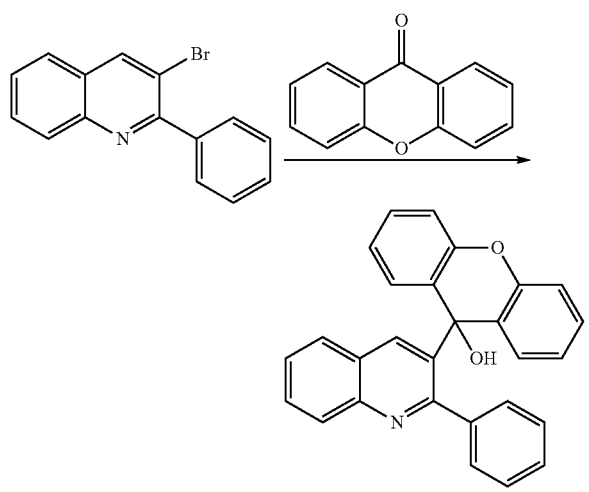

3-bromo-2-phenylquinoline (0.2 mmol, 57 mg) and anhydrous ether (2 ml) are added into a threk tube (15 ml), and nitrogen gas is used to replace the reaction atmosphere in the threk tube. After the mixture is stirred for 10 minutes at −78° C., 1.6 M n-butyllithium (0.2 mL) is added dropwise into the tube and reacts for 1 hour at −78° C. Xanthone (40 mg, 0.15 mmol) is dissolved in anhydrous ether (2 mL), and then atmosphere of the ether solution is replaced with nitrogen, then injected into the above reaction system dropwise with an injector, stirred for several minutes at −78° C., and then stirred overnight at room temperature. Subsequently, saturated ammonium chloride solution is added into the reaction system to quench the reaction, extraction is performed by using ethyl acetate (5 mL×3), the organic phases are combined, then washed with water and brine successively, dried with anhydrous Na$_2$SO$_4$, and filtered. The filtered solution is vacuum concentrated, and then purified through column chromatography to obtain a white solid (25 mg, yield 42%).

$^1$H-NMR (500 MHz, DMSO-d$^6$) δ 9.31 (s, 1H), 8.26 (d, J=8.1 Hz, 1H), 7.90 (d, J=8.3 Hz, 1H), 7.78 (dd, J=7.4, 7.6 Hz, 1H), 7.74 (dd, J=7.4, 7.6 Hz, 1H), 7.23 (dd, J=7.5, 7.6 Hz, 2H), 7.08-7.02 (m, 3H), 7.01-6.96 (m, 2H), 6.86 (s, 1H), 6.83 (d, J=8.3 Hz, 2H), 6.75 (dd, J=7.5, 7.6 Hz, 2H), 5.87 (d, J=7.6 Hz, 2H). MS (ESI): 402.16 [M+H]$^+$.

(2) Synthesis of Compound 3

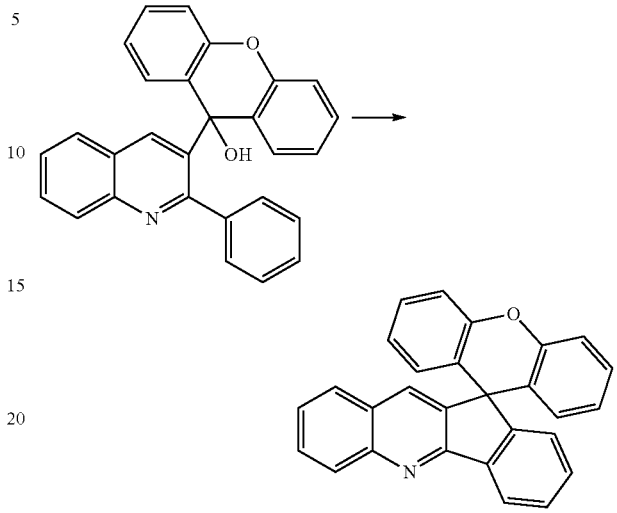

The precursor (30 mg, 0.07 mmol) of compound 3, acetic acid (1 mL), and 35% hydrochloric acid (0.25 mL) are added into a sealed tube (10 mL). The reaction solution is heated to 140° C. and stirred for 4 hours. After TLC shows that the reaction is finished, saturated NaHCO$_3$ solution is added to neutralize and quench the reaction. The reaction system is extracted with ethyl acetate (5 mL×3), the organic phases are combined, dried with anhydrous Na$_2$SO$_4$, filtered, concentrated, and purified through column chromatography to obtain a white solid (25 mg, yield 89.3%).

$^1$H-NMR (300 MHz, DMSO-d$^6$) δ 8.22 (d, J=7.5 Hz, 1H), 8.13 (d, J=8.3 Hz, 1H), 8.06 (s, 1H), 7.90 (d, J=7.9 Hz, 1H), 7.79-7.71 (m, 1H), 7.61-7.45 (m, 3H), 7.37-7.18 (m, 5H), 6.87-6.81 (m, 2H), 6.36 (d, J=8.1 Hz, 2H). MS (ESI): 384.14 [M+H]$^+$.

Synthesis Example 4: Synthesis of Compound 4

(1) Synthesis of Compound 4

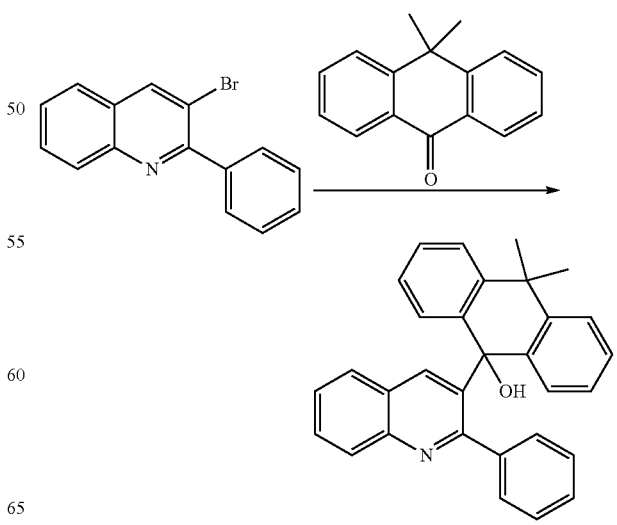

3-bromo-2-phenylquinoline (0.27 mmol, 76 mg) and anhydrous ether (2 ml) are added to a threk tube (15 ml), and nitrogen gas is used to replace the reaction atmosphere in the threk tube. After the mixture is stirred for 10 minutes at −78° C., 1.6 M n-butyllithium (0.27 mL) is added dropwise into the tube and reacts for 1 hour at −78° C. 10,10-dimethyl-anthrone (56.4 mg, 0.254 mmol) is dissolved in anhydrous ether (2 mL), and then atmosphere of the ether solution is replaced with nitrogen, then injected into the above reaction system dropwise with a injector, stirred for several minutes at −78° C., and then stirred overnight at room temperature. Subsequently, saturated ammonium chloride solution is added into the reaction system to quench the reaction, extraction is performed by using ethyl acetate (5 mL×3), the organic phases are combined, then washed with water and brine successively, dried with anhydrous $Na_2SO_4$, and filtered. The filtered solution is vacuum concentrated, and then purified through column chromatography to obtain a white solid (30 mg, yield 30%).

$^1$H-NMR (300 MHz, DMSO-d$^6$) δ 9.33 (s, 1H), 8.27 (d, J=9.0, 1.6 Hz, 1H), 7.90 (d, J=6.0 Hz, 1H), 7.82-7.66 (m, 2H), 7.37 (d, J=8.0 Hz, 2H), 7.31-7.21 (m, 2H), 7.15-7.06 (m, 2H), 6.99-6.89 (m, 3H), 6.71-6.62 (m, 2H), 6.09 (s, 1H), 5.79 (d, J=7.5 Hz, 2H), 1.43 (s, 3H), 1.05 (s, 3H). MS (ESI): 428.21 [M+H]$^+$.

(2) Synthesis of Compound 4

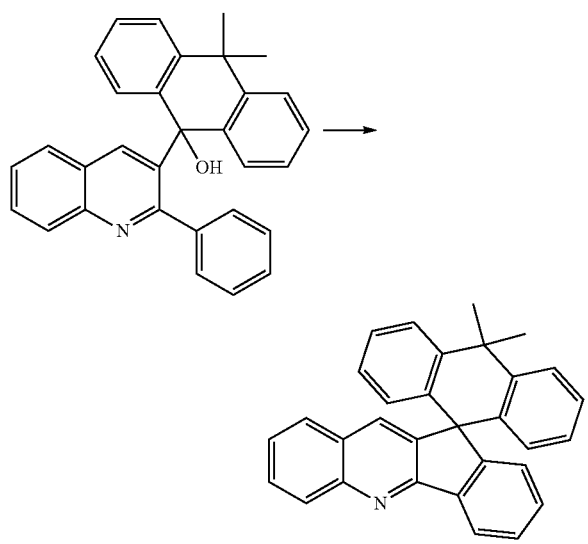

The precursor (43 mg, 0.1 mmol) of compound 4, suitable amount of polyphosphoric acid and methylbenzene (2 mL) are added into a sealed tube (10 mL). The reaction solution is heated to 120° C. and stirred for 4 hours. After TLC shows that the reaction is finished, the reaction solution is cooled to room temperature and poured into ice water to quench the reaction. Extraction is performed with ethyl acetate (10 mL-3), the organic phases are combined, washed with water and saturated $NaHCO_3$ solution (20 mL, 3) successively. The organic phase is dried with anhydrous $Na_2SO_4$, and filtered. The filtered solution is vacuum concentrated, and purified through column chromatography to obtain a white solid (38 mg, yield 92.7%).

$^1$H NMR (300 MHz, Chloroform-d) δ 8.23 (d, J=7.4 Hz, 1H), 8.14 (d, J=8.5 Hz, 1H), 7.86 (d, J=8.0 Hz, 1H), 7.83-7.70 (m, 4H), 7.55-7.47 (m, 2H), 7.44-7.39 (m, 1H), 7.26-7.21 (m, 2H), 6.96 (d, J=7.6 Hz, 1H), 6.90-6.85 (m, 2H), 6.19 (d, J=8.0, 2H), 1.97 (s, 3H), 1.93 (s, 3H). MS (ESI): 410.19 [M+H]$^+$.

Synthesis Example 5: Synthesis of Compound 5

(1) Synthesis of Ketone Fragment

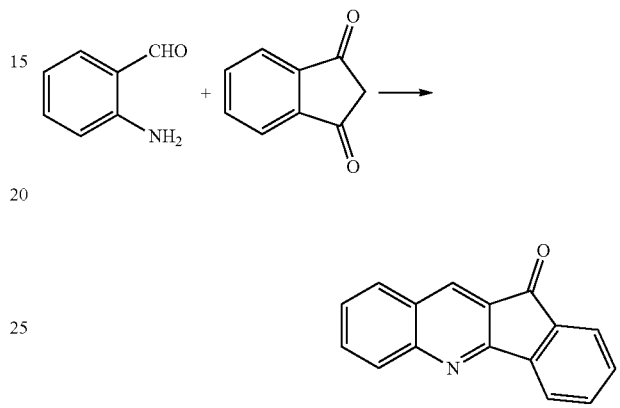

2-aminobenzaldehyde (1.21 g, 10 mmol), 1,3-indanedione (1.46 g, 10 mmol), and deionized water (50 mL) are added into a round-bottom flask (250 mL). The reaction solution is heated to 70° C. and stirred for 3 hours. After TLC shows that the reaction is finished, the reaction solution is cooled to room temperature, and extracted with ethyl acetate (50 mL×3). The organic phases are combined, washed with water, dried with anhydrous $Na_2SO_4$, and filtered. The filtered solution is vacuum concentrated, and purified through column chromatography to obtain a white solid (2.1 g, yield 92%).

$^1$H-NMR (300 MHz, DMSO-d$^6$) δ 8.61 (s, 1H), 8.15-7.98 (m, 3H), 7.84-7.77 (m, 3H), 7.64-7.60 (m, 2H).

(2) Synthesis of a Precursor of Compound 5

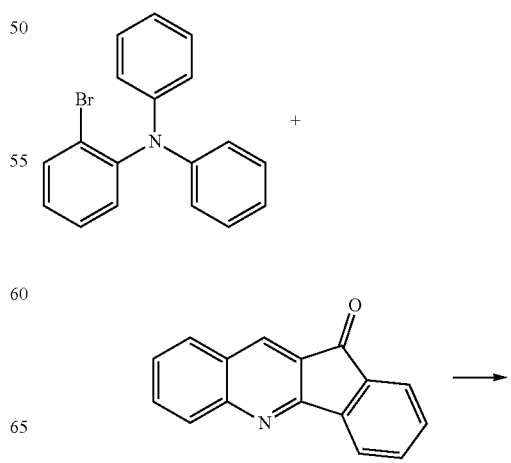

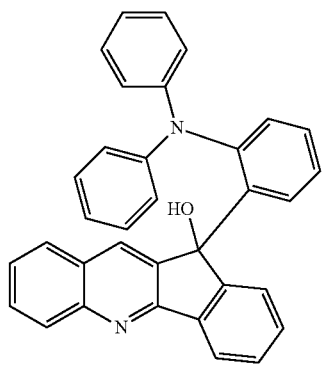

2-bromotriphenylamine (0.8 mmol, 260 mg) and anhydrous tetrahydrofuran (8 ml) are added into a threk tube (50 ml), and nitrogen gas is used to replace the reaction atmosphere in the threk tube. After the mixture is stirred for 10 minutes at −78° C., 1.6 M n-butyllithium (0.8 mL) is added dropwise into the tube and reacts for 1 hour at −78° C. The synthesized ketone fragment (185 mg, 0.8 mmol) is dissolved in anhydrous tetrahydrofuran (5 mL). After the atmosphere of the tetrahydrofuran solution is replaced with nitrogen, the solution is then injected into the above reaction system dropwise with an injected, stirred for several minutes at −78° C., and then stirred overnight at room temperature. After the reaction is finished, saturated ammonium chloride solution is added into the reaction system to quench the reaction, extraction is performed by using ethyl acetate (20 mL×3). The organic phases are combined, dried with anhydrous Na₂SO₄, filtered, vacuum concentrated, and then purified through silica gel column chromatography to obtain a yellow solid (164 mg, yield 43%).

¹H-NMR (300 MHz, DMSO-d⁶) δ 8.59 (d, J=7.9 Hz, 1H), 7.89 (d, J=8.4 Hz, 1H), 7.75 (dd, J=5.3, 3.2 Hz, 1H), 7.65-7.50 (m, 4H), 7.51-7.24 (m, 5H), 6.78-6.64 (m, 4H), 6.50-6.40 (m, 3H), 6.23-6.18 (m, 1H), 6.04 (d, J=8.4 Hz, 2H), 5.95 (d, J=7.9 Hz, 2H). MS (ESI): 477.20 [M+H]+.

(3) Synthesis of Compound 5

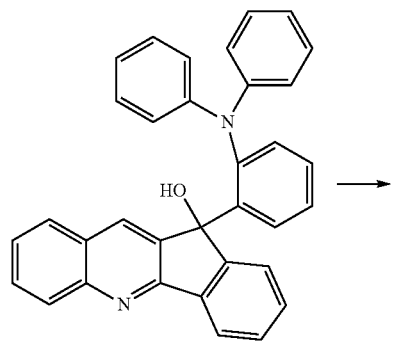

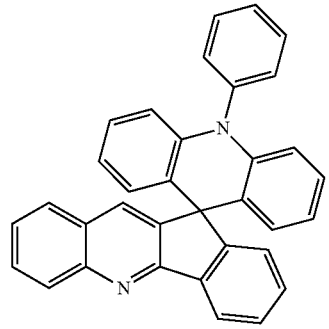

The precursor (476 mg, 1 mmol) of compound 5 and methane-sulfonic acid (5 mL) are added into a round-bottom flask (25 mL), and stirred for 30 minutes at room temperature. After TLC shows that the reaction is finished, saturated NaHCO₃ solution is added to neutralize the reaction solution. The reaction system is extracted with ethyl acetate (50 mL×3), the organic phases are combined, washed with water, dried with anhydrous Na₂SO₄, filtered, concentrated, and purified through column chromatography to obtain a white solid (407 mg, yield 89%).

¹H-NMR (500 MHz, DMSO-d⁶) δ 8.26 (s, 1H), 8.22 (d, J=7.5 Hz, 1H), 8.15 (d, J=8.3 Hz, 1H), 7.99 (d, J=7.9 Hz, 1H), 7.88-7.83 (m, 2H), 7.82-7.77 (m, 1H), 7.70-7.63 (m, 3H), 7.64-7.51 (m, 4H), 7.00-6.95 (m, 2H), 6.64-6.57 (m, 2H), 6.36-6.30 (m, 4H). MS (MALDI-TOF): 457.81 [M]+.

Synthesis Example 6: Synthesis of Compound 6

(1) Synthesis of Compound 6

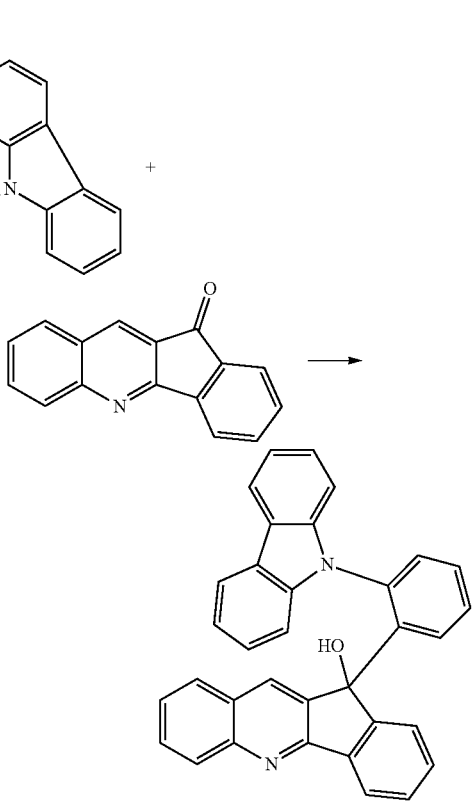

9-(2-bromophenyl)carbazole (0.8 mmol, 260 mg) and anhydrous tetrahydrofuran (8 ml) are added into a threk tube (50 mL), and nitrogen gas is used to replace the reaction atmosphere in the threk tube. After the mixture is stirred for 10 minutes at −78° C., 1.6 M n-butyllithium (0.8 mL) is added dropwise into the tube and reacts for 1 hour at −78° C. The ketone fragment (185 mg, 0.8 mmol) is dissolved in anhydrous tetrahydrofuran (5 mL), then atmosphere of the tetrahydrofuran solution is replaced with nitrogen, the solution is then injected into the above reaction system dropwise with an injector, stirred for several minutes at −78° C., and then stirred overnight at room temperature. Subsequently, saturated ammonium chloride solution is added into the reaction system to quench the reaction, extraction is performed by using ethyl acetate (20 mL 3). The organic phases are combined, washed with water, dried with anhydrous Na$_2$SO$_4$, filtered, vacuum concentrated, and then purified through column chromatography to obtain a yellow solid (164 mg, yield 43%).

$^1$H-NMR (300 MHz, DMSO-d$^6$) δ 8.77 (d, J=8.1 Hz, 1H), 7.92 (s, 1H), 7.89-7.84 (m, 1H), 7.74 (d, J=7.7 Hz, 1H), 7.66 (d, J=7.9 Hz, 1H), 7.61-7.44 (m, 4H), 7.40-7.28 (m, 2H), 7.22-7.14 (m, 1H), 7.08-6.88 (m, 4H), 6.77-6.69 (m, 1H), 6.52 (s, 1H), 6.50-6.41 (m, 1H), 6.41-6.32 (m, 1H), 6.06 (d, J=8.1 Hz, 1H), 5.84 (d, J=8.0 Hz, 1H). MS (ESI): 475.18 [M+H]$^+$.

(2) Synthesis of Compound 6

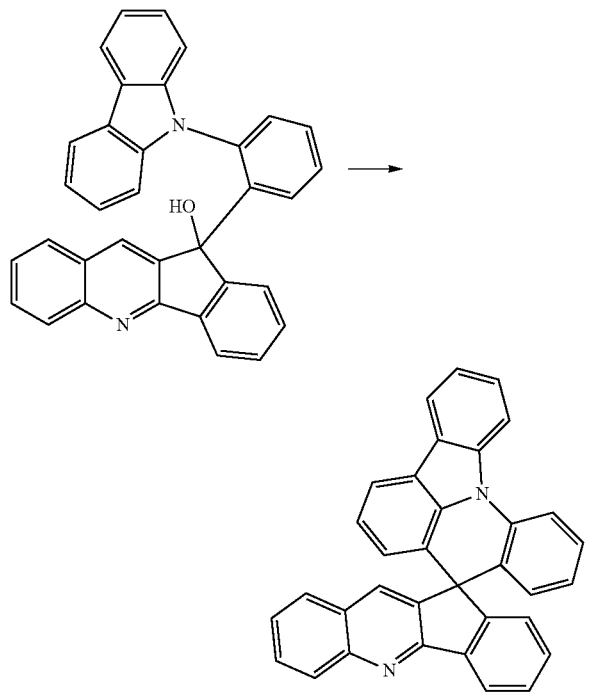

The precursor of (474 mg, 1 mmol) of compound 6 and methane-sulfonic acid (5 mL) are added into a round-bottom flask (25 mL), and stirred for 30 minutes at room temperature. After TLC shows that the reaction is finished, saturated NaHCO$_3$ solution is added to neutralize the reaction solution. The reaction system is extracted with ethyl acetate (50 mL×3), the organic phases are combined, washed with water, dried with anhydrous Na$_2$SO$_4$, filtered, vacuum concentrated, and purified through column chromatography to obtain a white solid (420 mg, yield 92%).

$^1$H-NMR (300 MHz, Chloroform-d) δ 8.54 (d, J=8.5 Hz, 1H), 8.44 (d, J=8.6 Hz, 1H), 8.37 (d, J=7.8 Hz, 1H), 8.27 (d, J=7.3 Hz, 1H), 8.16 (d, J=8.4 Hz, 1H), 8.10-8.03 (m, 2H), 7.84 (d, J=8.1 Hz, 1H), 7.79-7.68 (m, 2H), 7.83-7.55 (m, 1H), 7.55-7.41 (m, 4H), 7.22 (d, J=7.5 Hz, 1H), 7.15-7.07 (m, 1H), 6.97-6.89 (m, 1H), 6.55 (d, J=6.6 Hz, 1H), 6.45 (d, J=7.6 Hz, 1H). MS (MALDI-TOF): 455.81 [M]$^+$.

Synthesis Example 7: Synthesis of Compound 7

(1) Synthesis of a Precursor of Compound 7

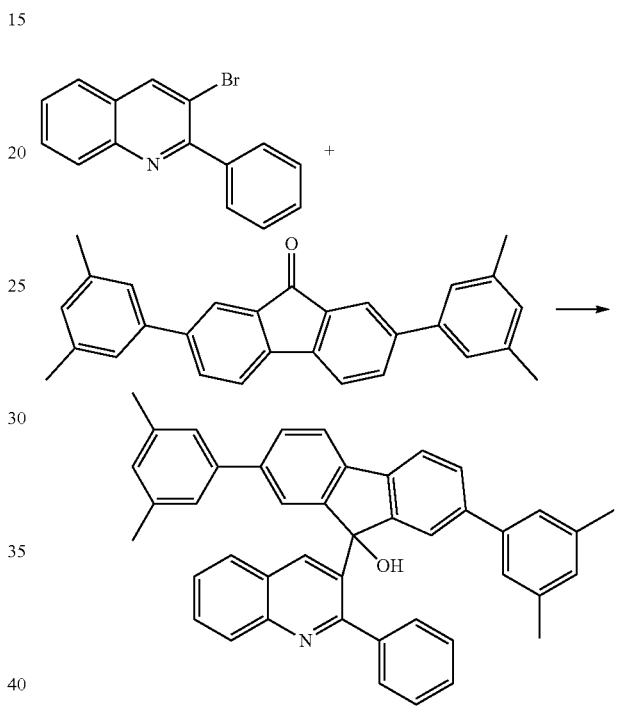

3-bromo-2-phenylquinoline (1 mmol, 284 mg) and anhydrous ether (5 ml) are added into a threk tube (50 ml), and nitrogen gas is used to replace the reaction atmosphere in the threk tube. After the mixture is stirred for 10 minutes at −78° C., 1.6 M n-butyllithium (1 mL) is added dropwise into the tube and reacts for 1 hour at −78° C. The corresponding ketone fragment (194 mg, 0.5 mmol) is dissolved into anhydrous ether (10 mL), then atmosphere of the ether solution is replaced with nitrogen, the solution is then injected into the above reaction system dropwise with an injector, stirred for several minutes at −78° C., and then stirred overnight at room temperature. Subsequently, saturated ammonium chloride solution is added into the reaction system to quench the reaction, extraction is performed by using ethyl acetate (30 mL×3). The organic phases are combined, washed with water, dried with anhydrous Na$_2$SO$_4$, filtered, vacuum concentrated, and then purified through column chromatography to obtain a milk white solid (110 mg, yield 37%).

$^1$H-NMR (300 MHz, DMSO-d$^6$) δ 9.39 (s, 1H), 8.26 (d, J=9.0, 1H), 7.89 (d, J=8.2 Hz, 1H), 7.80-7.65 (m, 2H), 7.53 (dd, J=7.9, 1.7 Hz, 2H), 7.41-7.31 (m, 4H), 7.21 (d, J=1.6 Hz, 4H), 6.97-6.90 (m, 3H), 6.70-6.62 (m, 2H), 6.55 (s, 1H), 6.00 (d, J=7.9, 2H), 2.29 (s, 12H). MS (ESI): 594.28 [M+H]$^+$.

(2) Synthesis of Compound 7

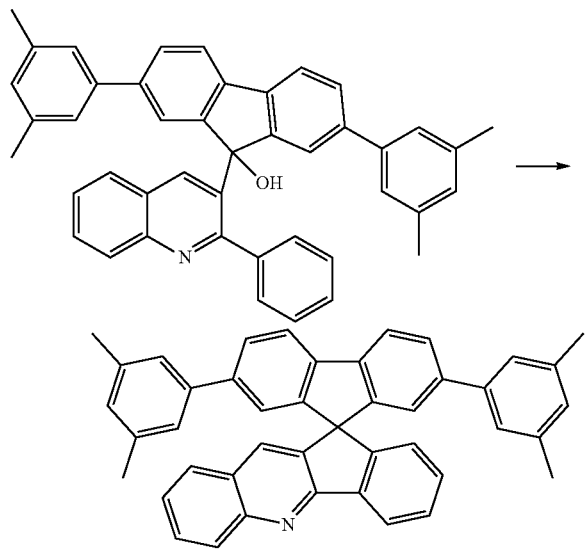

The precursor (59 mg, 0.1 mmol) of compound 7 and methane-sulfonic acid (1 mL) are added into a round-bottom flask (25 mL), and stirred for 10 minutes at room temperature. After TLC shows that the reaction is finished, saturated NaHCO$_3$ solution is added to neutralize the reaction solution. The reaction system is extracted with ethyl acetate (20 mL×3), the organic phases are combined, washed with water, dried with anhydrous Na$_2$SO$_4$, filtered, concentrated, and purified through column chromatography to obtain a white solid (52 mg, yield 91%).

$^1$H-NMR (300 MHz, Chloroform-d$^6$) δ 8.39 (d, J=7.8 Hz, 1H), 8.25 (d, J=8.5 Hz, 1H), 7.94 (d, J=8.0 Hz, 2H), 7.74-7.63 (m, 3H), 7.62-7.56 (m, 2H), 7.55-7.48 (m, 1H), 7.47-7.39 (m, 1H), 7.34-7.34 (m, 1H), 7.05-6.86 (m, 9H), 2.26 (s, 12H). MS (ESI): 576.27 [M+H]$^+$.

An embodiment of the present disclosure further provides an organic electronic assembly. The organic electronic assembly contains at least one organic photoelectric functional material. The organic electronic assembly is organic light-emitting diode, light-emitting diode, compact fluorescent lamp, incandescent lamp, organic photovoltaic cell, or organic field effect transistor.

An embodiment of the present disclosure further provides an use of the organic photoelectric functional material as a host material or as an electron transporting-type host material in a co-host system in an organic electronic assembly.

An embodiment of the present disclosure further provides a use of the organic photoelectric functional material as biomarker or in imaging techniques. For example, the organic photoelectric functional material is used in biological applications, and as luminescent label in an anti-cancer agent.

An embodiment of the present disclosure further provides an light-emitting device. The light-emitting device includes a cathode, an anode, and at least one organic layer placed between the cathode and the anode, the organic layer containing the organic photoelectric functional material. The organic layer generally contains a hole transporting-type host material, an electron transporting-type host material, and a doping material. The compound provided in the present disclosure may be used as the electron transporting-type host material. In an specific embodiment, the compound of the present disclosure is used as the electron transporting-type host material, which, together with a hole transporting-type host material and a phosphorescent doping material, forms an organic layer of an OLED device, the hole transporting-type host material having LUMO is at least 0.1 eV higher than that of the compound. The electron transporting-type host material of the present disclosure and the hole transporting-type host material whose LUMO is at least 0.1 eV higher are excited to form an exciplex. The energy difference between a singlet state and a triplet state of the formed exciplex is smaller than 0.15 eV. In the meantime, the energy of a triplet state of the phosphorescent doping material is lower than energy of the triplet state of the exciplex, achieving a good energy transfer effect. When a fluorescent doping material is selected for forming the organic layer, the energy of a singlet state of the selected fluorescent doping material shall be lower than the energy of the singlet state of the formed exciplex, in order to achieve good energy transfer effect.

The compounds provided in the present disclosure are applicable for various optical devices and photoelectric devices, including but not limited to, light-absorbing devices such as solar sensitive device and light sensitive device, organic light-emitting diode (OLED), light-emitting device, devices having both light-absorbing capability and light-emitting capability, and labels used in biological applications.

An embodiment of the present disclosure further provides a bipolar host material. The bipolar host material is at least one of the organic photoelectric functional materials provided in the present disclosure.

An embodiment of the present disclosure further provides an electron transporting-type host material, and the electron transporting-type host material is at least one of the organic photoelectric functional materials provided in the present disclosure.

As mentioned above, the compounds provided in the present disclosure are pure organic compounds. On one hand, the compounds may be used as a fluorescent emitter, a delayed fluorescent emitter, or a phosphorescent emitter.

On the other hand, these compounds may be used independently as the bipolar host material, i.e., having both good electron transportation property and good hole transportation property, good for charge balance of carriers, thereby achieving high luminous efficiency; or these compounds are used as an electron transporting-type host material which, together with a hole transporting-type host material, forms a co-host system, for example, applied in an OLED device such as a full-color displayer.

In an embodiment, the compound is used in an organic light-emitting diode (OLED) 1000. The structure of the OLED 1000 is schematically shown in the FIGURE. As shown in the FIGURE OLED 1000 includes a substrate 1002, an anode 1004, a hole transporting layer (HTL) 1006, a light-emitting functional layer 1008, an electron transporting layer (ETL) 1010, and a metal cathode layer 1012. The anode 1004 is generally made of a transparent material, for example, indium tin oxide. The light-emitting functional layer 1008 may be a light-emitting material layer (EML) which only contains an emitter, or contains both an emitter and a host or a co-host. Any one or more layers shown in the FIGURE may contain indium tin oxide (ITO), MoO$_3$, Ni$_2$O$_3$, poly(3,4-ethylenedioxythiophene)(PEDOT), polystyrene sulfonate (PSS), NHT-49, NHT-51, 2,3,5,6-tetrafluoro-7,7',8,8'-tetracyanodimethyl-p-benzoquinone (F4-TCNQ), N,N'-di-1-naphthyl-N,N'-diphenyl-1,1'-biphenyl-4, 4'-diamine (NPD), 4,4'-cyclohexyl bis[N,N-di(4-methylphenyl) aniline] (TAPC), 2,6-bis(N-carbazolyl)-pyridine (mCpy), 2,8-bis(diphenylphosphoryl) dibenzothiophene (PO15), LiF, LiQ, $Cs_2CO_3$, $CaCO_3$, Al, or combinations thereof.

In an embodiment, the light-emitting functional layer 1008 may contain one or more compounds provided by the present disclosure, and optionally contain a hole-type host material. The hole-type host material may be any suitable host material in the related art.

In an embodiment, the electron transporting layer 1010 and the hole transporting layer 1006 may also contain one or more compounds provided by the present disclosure, and may further contain an injection layer close to the electrode.

The injection layer includes an electron injection layer (EIL) and a hole injection layer (HIL). These injection layers may be formed as a single layer or distributed separately in the transporting layer.

Emission color of the OLED depends on emission energy (optical band gap) of the light-emitting functional layer 1008. The emission energy (optical band gap) of the light-emitting functional layer 1008 can be tuned by adjusting the emitter compound, the host material or the electron structure thereof. The electron transporting material in the electron transporting layer 1010 may be any suitable electron transporting material in the related art, or the hole transporting material in the hole transporting layer 1006 may be any suitable hole transporting material in the related art. Both the electron transporting material in the electron transporting layer 1010 and the hole transporting material in the hole transporting layer 1006 can be selected in the related art for achieving a better effect.

The compound listed in present disclosure may be blended with a small molecule hole transporting-type host material to form an exciplex. If a photoluminescence spectrum of the blend has an obvious red shift with respect to the photoluminescence spectrum of any component of the blend, it demonstrates that an exciplex is formed.

TABLE 1

| Hole transporting-type host material | Electron transporting-type host material of the present disclosure | Band gap of exciplex (eV) | Emission peak (nm) | Emission range of exciplex (nm) |
|---|---|---|---|---|
| TCTA | compound 3 | 3.22 | 410 | 360-590 |
| TCTA | compound 4 | 3.28 | 412 | 360-550 |
| TCTA | compound 5 | 3.29 | 485 | 360-610 |
| TCTA | compound 6 | 3.23 | 412 | 360-600 |
| TAPC | compound 3 | 3.02 | 460 | 360-580 |
| TAPC | compound 4 | 3.08 | 447 | 360-580 |
| TAPC | compound 5 | 3.09 | 483 | 350-610 |
| TAPC | compound 6 | 3.02 | 467 | 350-600 |
| MCP | compound 3 | 3.37 | 374 | 350-470 |
| MCP | compound 4 | 3.38 | 378 | 355-550 |
| MCP | compound 5 | 3.39 | 487 | 360-610 |
| MCP | compound 6 | 3.33 | 390 | 355-610 |

Table 1 shows photoluminescence spectrum data of co-vapor deposited films formed by compounds 3-6 and the hole transporting-type host materials (molar ratio 1:1). The new emission peaks generated due to charge transfer of the exciplexes are different from both the emission peak of the electron transporting-type host material component and the emission peak of the hole transporting-type host material component. Compounds 3-6 have narrow photoluminescence spectra in a range of 360-380 nm due to local π-π* electron transfer, while the wide spectra in a range of 400 nm or greater of the exciplexes are generated due to electron transfer in the molecules.

As described above, the OLED device provided in the present disclosure includes the cathode, the anode, and the organic layer between the cathode and the anode. The organic layer generally includes the hole-transporting host material, the electron-transporting host material, and the doping material. The electron-transporting host material may use the organic photoelectric functional compounds of the present disclosure. The electron-transporting host material and the hole-transporting host material may be excited to form an exciplex as a co-host. The energy difference between a singlet state and a triplet state of the formed exciplex is less than 0.15 eV The doping material may be a fluorescent material or a phosphorescent material. The energy of the triplet state of the phosphorescent doping material shall be lower than the energy of the triplet state of the exciplex.

For example, the formed host material may be blended with iridium-based phosphorescent doping material, such as (acetylacetone)bis(2-phenylquinoline) iridium ($Ir(PQ)_2$ acac), and bis(2-(3,5-dimethylphenyl)quinoline-C2,N') (acetylacetonato) iridium (III) ($Ir(DMPQ)_2$acac), thereby improving efficiency of the phosphorescent OLED device.

Further, the organic layer may include a light-emitting layer, a hole transporting layer between the anode and the light-emitting layer, and an electron transporting layer between the cathode and the light-emitting layer.

The compounds listed in the present disclosure may independently form the electron transporting layer or may be used as a part of the material for forming the electron transporting layer. If the compound is used as a part of the material for forming the electron transporting layer, preferably, the compound of the present disclosure is doped by at least 30 wt % based on the total weight of the material for forming the electron transporting layer, more preferably at least 50 wt %.

The hole transporting layer is made of a hole transporting material, and the hole transporting material may be the same as the hole transporting-type host material. The electron transporting layer is made of an electron transporting, and the electron transporting material may be the same as the electron transporting-type host material.

The light-emitting layer may only contain the emitter provided by the present disclosure, or contain both the emitter and the host or co-host.

The co-host material formed by the compound of the present disclosure and another hole transporting-type host material may be used to assembly the organic layer in the device in a solution manner or in a vapor-deposition manner. The device formed in the vapor-deposition manner may have the following structure of material layers (the material layers are separated from one another with "/", "nm" represents a thickness unit of each layer): indium tin oxide/

HAT-CN(10 nm)/4,4'-cyclohexyl bis[N,N-di(4-methylphenyl) aniline](TAPC) or 4,4',4''-tris(carbazole-9-yl)triphenylamine (TCTA) (40 nm)/TAPC or TCTA electron transporting-type host (i.e., the compound of the present disclosure) red light dopant (20 nm)/1,3,5-tris[(3-pyridyl)-3-phenyl]benzene (TmPyPB)(60 nm)/8-hydroxylquinolinolato-lithium (1 nm)/aluminum (100 nm). The device formed in the solution manner may have the following structure of layers: indium tin oxide/PEDOT:PSS (40 nm)/TCTA or TAPC:electron transporting-type host (i.e., the compound of the present disclosure): red light dopant (60 nm)/TmPyPB (60 nm)/8-hydroxylquinolinolato-lithium (1 nm)/aluminum (100 nm). In both the vapor-deposition manner and the solution manner, the indium tin oxide substrate needs to be cleaned with acetone, ultrapurified water, ethanol and ultrasonic treatment, then blown to dry with a nitrogen gun and then exposed to UV-ozone. Subsequently, the organic layers are successively vapor-deposited onto the indium tin oxide substrate under vacuum (<$10^{-5}$ Pa), or successively spin coated onto the indium tin oxide substrate in the solution manner. The inorganic layer is later etched into the device using a mask (<$10^{-5}$ Pa). The relation between current density and voltage and the relation between luminous intensity and voltage were measured by using Keithley source measure unit 2400 and spectrascan spectrometer PR735.

TABLE 2

| Device preparing method | Co-host layer (hole transporting + electron transporting) | Turn-on voltage (V) | Luminous efficiency (Cd/A) (1000 cd/m$^2$) | External quantum efficiency (%) (1000 cd/m$^2$) | Power efficiency (L/W) (1000 cd/m$^2$) |
| --- | --- | --- | --- | --- | --- |
| Vapor-deposition manner | TCTA + compound 3 | 2.6 | 13.5 | 11.1 | 10.5 |
| Vapor-deposition manner | TCTA + compound 4 | 3.2 | 13.0 | 10.6 | 9.2 |
| Vapor-deposition manner | TCTA + compound 5 | 2.6 | 13.8 | 13.1 | 10.4 |
| Vapor-deposition manner | TCTA + compound 6 | 3.2 | 12.3 | 11.2 | 9.7 |

In Table 2, luminous efficiency (Cd/A), external quantum efficiency (%), and power efficiency (L/W) are device efficiencies measured under a brightness of 1000 cd/m$^2$.

From the data above and the comparison results, it can be concluded that the devices assembled by the compounds provided by the present disclosure have low turn-on voltage, high luminous efficiency, and high device efficiencies even under high luminous intensity.

Based on the disclosed contents in the present disclosure, those killed in the art can make modifications and obtain other embodiments. Therefore, this description is merely exemplary for illustration. The elements and materials explained in the present disclosure may be substituted by other elements and materials, the components and procedures may be reverted, and specific features may be applied independently, which shall fall into the protection scope of the present disclosure. Those skilled in the art may make modifications to the elements explained in the present disclosure, without departing from the principles and scope of the present disclosure.

What is claimed is:

1. An organic photoelectric functional material selected from the group consisting of the following compounds and combination thereof:

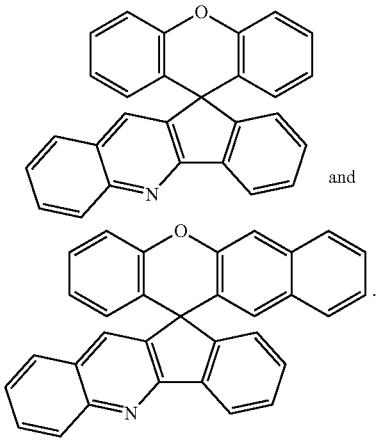

and.

2. An organic electronic assembly, comprising the organic photoelectric functional material according to claim 1.

3. The organic electronic assembly according to claim 2, wherein the organic electronic assembly is selected from a group consisting of organic light-emitting diode, light-emitting diode, compact fluorescent lamp, incandescent lamp, organic photovoltaic cell, and organic field effect transistor.

4. A light-emitting device, comprising a cathode, an anode, and at least one organic layer placed between the cathode and the anode, wherein the organic layer comprises the organic photoelectric functional material according to claim 1.

5. A host material, a bipolar host material, or an electron-transporting host material in a co-host material system in an organic electronic assembly comprising the organic photoelectric functional material according to claim 1.

6. A bipolar host material comprising the organic photoelectric functional material according to claim 1.

7. An electron transmission host material comprising the organic photoelectric functional material according to claim 1.

* * * * *